US008926662B2

(12) United States Patent
Perriello et al.

(10) Patent No.: US 8,926,662 B2
(45) Date of Patent: Jan. 6, 2015

(54) TISSUE GRAFT ANCHORING

(75) Inventors: Michael James Perriello, Hopedale, MA (US); Alfred Rodrigue Berube, North Attleboro, MA (US); Michael Charles Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 74 days.

(21) Appl. No.: 13/363,575

(22) Filed: Feb. 1, 2012

(65) Prior Publication Data
US 2013/0197580 A1    Aug. 1, 2013

(51) Int. Cl.
*A61B 17/04* (2006.01)

(52) U.S. Cl.
USPC .......................................................... 606/232

(58) Field of Classification Search
CPC ............................................. A61B 2017/0446
USPC ..................................... 606/232; 289/1.2, 1.5
See application file for complete search history.

(56) References Cited

U.S. PATENT DOCUMENTS

| | | |
|---|---|---|
| 3,580,256 A | 5/1971 | Wilkinson et al. |
| 4,605,414 A | 8/1986 | Czajka |
| 5,139,520 A | 8/1992 | Rosenberg |
| 5,217,470 A | 6/1993 | Weston |
| 5,234,445 A | 8/1993 | Walker et al. |
| 5,306,301 A | 4/1994 | Graf et al. |
| 5,405,352 A | 4/1995 | Weston |
| 5,449,367 A | 9/1995 | Kadry |
| 5,451,203 A | 9/1995 | Lamb |
| 5,527,341 A | 6/1996 | Gogolewski et al. |
| 5,645,588 A | 7/1997 | Graf et al. |
| 5,718,717 A | 2/1998 | Bonutti |
| 5,769,894 A | 6/1998 | Ferragamo |
| 5,893,592 A | 4/1999 | Schulze et al. |
| 5,989,252 A | 11/1999 | Fumex |
| 6,143,029 A | 11/2000 | Rippstein |
| 6,193,754 B1 | 2/2001 | Seedhom |
| 6,296,659 B1 | 10/2001 | Foerster |
| 6,517,578 B2 | 2/2003 | Hein |

(Continued)

FOREIGN PATENT DOCUMENTS

| | | |
|---|---|---|
| EP | 328401 A1 | 8/1989 |
| EP | 0598219 A2 | 5/1994 |

(Continued)

OTHER PUBLICATIONS

"Technique for ACL Reconstruction with Acufex® Director Drill Guide and Endobutton® CL," Copyright 1999, Smith & Nephew, Inc., 20 pages.

(Continued)

*Primary Examiner* — Katherine Dowe
*Assistant Examiner* — Michael Mendoza
(74) *Attorney, Agent, or Firm* — Chapin IP Law, LLC

(57) ABSTRACT

A fixation device includes a member defining at least two openings, and a suture tied to the member by passing the suture through the at least two openings in the member to form two suture loops through which ends of the suture pass. The two suture loops are interconnected. A method of securing a tissue graft includes providing the fixation member, attaching the suture to a tissue graft, and adjusting the length of the suture between the fixation member and the tissue graft by pulling the suture.

13 Claims, 8 Drawing Sheets

(56) References Cited

U.S. PATENT DOCUMENTS

| | | | |
|---|---|---|---|
| 6,652,561 | B1 | 11/2003 | Tran et al. |
| 7,601,165 | B2 | 10/2009 | Stone |
| 7,651,509 | B2 * | 1/2010 | Bojarski et al. ............... 606/139 |
| 7,658,751 | B2 | 2/2010 | Stone et al. |
| 7,749,250 | B2 | 7/2010 | Stone et al. |
| 7,905,904 | B2 | 3/2011 | Stone et al. |
| 8,137,382 | B2 | 3/2012 | Denham et al. |
| 2001/0041938 | A1 | 11/2001 | Hein |
| 2002/0029066 | A1 | 3/2002 | Foerster |
| 2002/0115999 | A1 | 8/2002 | McDevitt et al. |
| 2002/0173788 | A1 | 11/2002 | Bojarski et al. |
| 2003/0050666 | A1 | 3/2003 | Grafton |
| 2004/0181234 | A1 | 9/2004 | McDevitt et al. |
| 2004/0220573 | A1 | 11/2004 | McDevitt et al. |
| 2005/0149118 | A1 | 7/2005 | Koyfman et al. |
| 2005/0251159 | A1 | 11/2005 | Ewers et al. |
| 2005/0251205 | A1 | 11/2005 | Ewers et al. |
| 2005/0277985 | A1 | 12/2005 | Wert et al. |
| 2006/0155328 | A1 | 7/2006 | Foerster |
| 2006/0190041 | A1 | 8/2006 | Fallin et al. |
| 2007/0010857 | A1 | 1/2007 | Sugimoto et al. |
| 2007/0016244 | A1 | 1/2007 | Behl et al. |
| 2007/0156174 | A1 | 7/2007 | Kaiser et al. |
| 2007/0162125 | A1 | 7/2007 | LeBeau et al. |
| 2007/0239209 | A1 | 10/2007 | Fallman |
| 2008/0027446 | A1 | 1/2008 | Stone et al. |
| 2008/0065114 | A1 | 3/2008 | Stone et al. |
| 2008/0082128 | A1 | 4/2008 | Stone |
| 2008/0177336 | A1 | 7/2008 | Cerundolo |
| 2008/0195148 | A1 | 8/2008 | Cook et al. |
| 2008/0208204 | A1 | 8/2008 | Schmieding et al. |
| 2008/0208252 | A1 | 8/2008 | Holmes |
| 2008/0255613 | A1 | 10/2008 | Kaiser et al. |
| 2008/0312689 | A1 | 12/2008 | Denham et al. |
| 2009/0036905 | A1 | 2/2009 | Schmieding |
| 2009/0062846 | A1 | 3/2009 | Ken |
| 2009/0082805 | A1 | 3/2009 | Kaiser et al. |
| 2009/0306711 | A1 | 12/2009 | Stone et al. |
| 2009/0312776 | A1 | 12/2009 | Kaiser et al. |
| 2009/0318961 | A1 | 12/2009 | Stone et al. |
| 2010/0023056 | A1 | 1/2010 | Johansson et al. |
| 2010/0114163 | A1 | 5/2010 | Martin |
| 2010/0145384 | A1 | 6/2010 | Stone et al. |
| 2010/0256677 | A1 | 10/2010 | Albertorio et al. |
| 2010/0268273 | A1 | 10/2010 | Albertorio et al. |
| 2010/0268275 | A1 | 10/2010 | Stone et al. |
| 2011/0022083 | A1 | 1/2011 | DiMatteo et al. |
| 2011/0022084 | A1 | 1/2011 | Sengun et al. |
| 2011/0098728 | A1 | 4/2011 | McDevitt et al. |
| 2011/0152885 | A1 | 6/2011 | McDevitt et al. |
| 2011/0152929 | A1 | 6/2011 | McDevitt et al. |
| 2011/0264141 | A1 | 10/2011 | Denham et al. |
| 2012/0109194 | A1 | 5/2012 | Miller et al. |
| 2012/0123541 | A1 | 5/2012 | Albertorio et al. |

FOREIGN PATENT DOCUMENTS

| | | |
|---|---|---|
| FR | 2743294 A1 | 7/1997 |
| GB | 2370227 B | 11/2002 |
| WO | WO03092551 A1 | 11/2003 |
| WO | WO2007005394 A1 | 1/2007 |
| WO | WO2009029914 A1 | 3/2009 |

OTHER PUBLICATIONS

"Endobutton Direct: Fixation Device," Smith & Nephew, Inc., reprinted from http://global.smith-nephew.com/us/product23376_5895.htm, on Nov. 22, 2010, 3 pages.

"EndoButton* CL," Smith & Nephew, Inc., reprinted from http://endo.smith nephew.com/es/Standard.asp? NodeID=2715, on Nov. 22, 2010, 1 page.

Fromm, Stuart, "ACL Reconstruction with Bone-Tendon-Bone Transplants using the Endobutton CL BTB Fixation System," Smith & Nephew, Inc., Copyright 2004, printed on Apr. 4, 11 pages.

Scope This Out, vol. 10, No. 2, Summer 2008, 8 pages.

Scope This Out, vol. 12, No. 2, Fall 2010, 8 pages.

Scope This Out, vol. 12, No. 1, Spring 2010, 8 pages.

ToggleLoc™: Femoral Fixation Device with Zip Loop Technology, Biomet Sports Medicine, Inc., 2007, 8 pages.

Glousman, Ronald, et al, "JuggerKnot™ Soft Anchor Surgical Technique," Biomet Sports Medicine, 2010, 1 page.

Game Plan: Innovative Products to be Launched AAOS 2010, Biomet Sports Medicine, Spring 2010, vol. 2, No. 3, 1 page.

Lawhorn, Keith, "MaxFire™ MarXmen™ Device Surgical Technique:," Biomet Sports Medicine, 2010, 1 page.

Invitation to Pay Additional Fees and Communication Relating to the Results of the Partial International Search for International Application No. PCT/US2012/023056, mailed Apr. 16, 2012.

International Search Report and Written Opinion for International Application No. PCT/US2012/023056, mailed Jun. 13, 2012.

International Search Report, PCT/US2013/024231, Jun. 10, 2013, pp. 2.

* cited by examiner

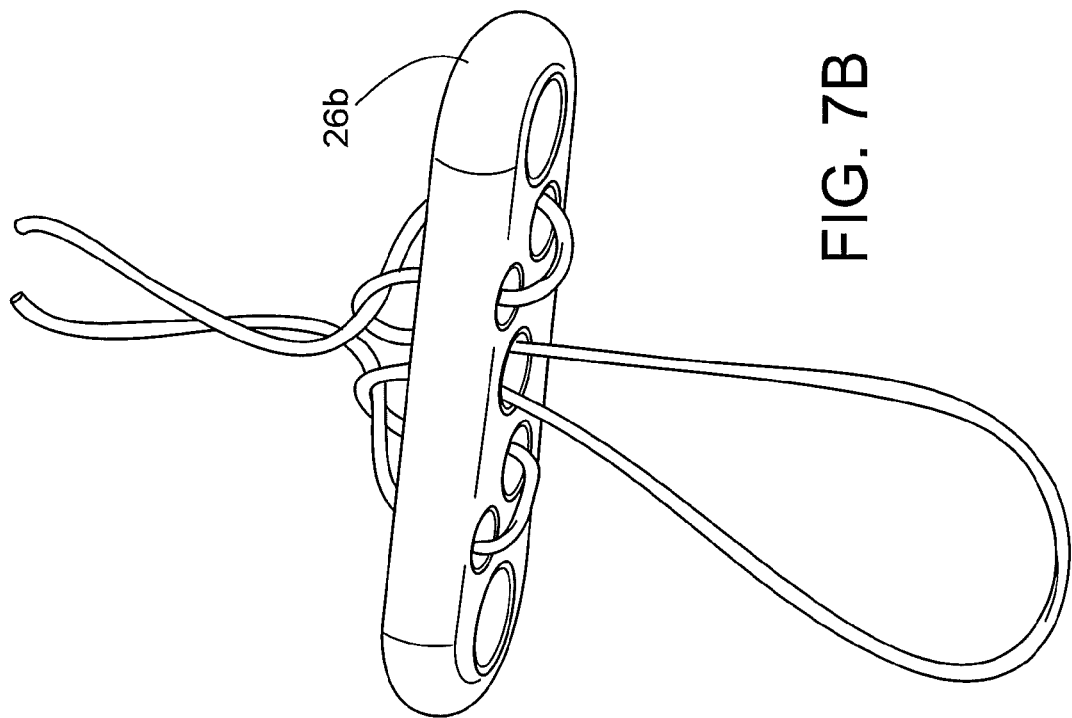
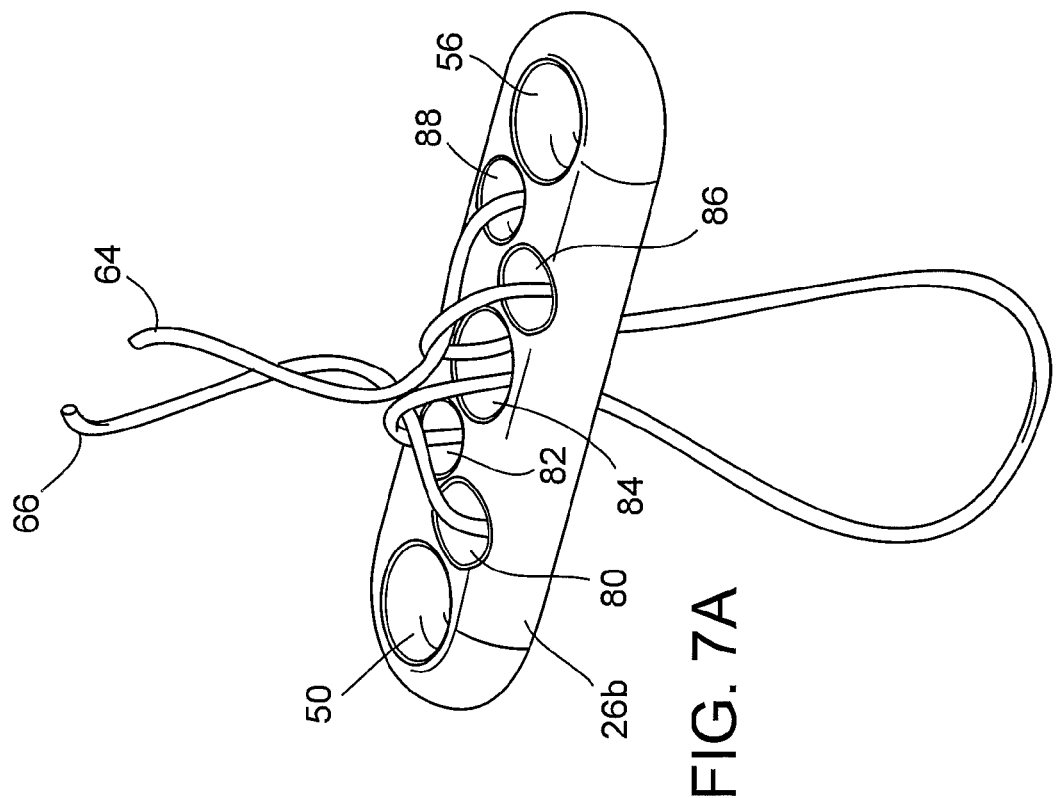
FIG. 7A
FIG. 7B

TISSUE GRAFT ANCHORING

This invention relates to tissue graft anchoring.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

It is also known to use a graft fixation member, e.g., a fixation button, to secure the tissue graft at the femoral cortex, as described in U.S. Pat. No. 5,306,301 ("the '301 patent") hereby incorporated by reference in its entirety. When using a fixation button, the femoral passage generally includes a relatively larger diameter portion for receiving the graft, and a smaller diameter, passing channel near the femoral cortex for receiving a length of suture that runs from the tissue graft to the fixation button. By measuring the total length of the femoral passage and the length of the larger diameter portion of the femoral passage, the surgeon determines the appropriate length of suture material for attaching the fixation button to the tissue graft.

SUMMARY

To increase the graft/channel interface in femoral fixation for cruciate repair the distance between a graft fixation member and the tendon construct is reduced. The ability to minimize this distance is generally limited by fixation member flipping constraints, which results in less tendon in the femoral channel, or leads to making compromises in the size of the graft fixation member to accommodate the tendon and the flipping of the graft fixation member.

According to one aspect, a method of securing a tissue graft includes providing a fixation member having a suture tied thereto by passing the suture through at least two openings in the fixation member to form two suture loops through which ends of the suture pass, attaching the suture to the tissue graft, and adjusting the length of the suture between the fixation member and the tissue graft by pulling the suture.

Embodiments of this aspect may include one or more of the following features.

The two suture loops are interconnected. Attaching the suture includes forming a loop of soft tissue of the tissue graft over the suture. Attaching the suture includes passing the suture through a bone block of the tissue graft followed by tying the suture to the fixation member. The method includes passing the fixation member, suture, and attached tissue graft through a bone passage, followed by adjusting the length of the suture between the fixation member and the tissue graft.

According to another aspect, a fixation device includes a member defining at least two openings, and a suture tied to the member by passing the suture through the at least two openings in the member to form two suture loops through which ends of the suture pass.

Embodiments of this aspect may include one or more of the following features.

The two suture loops are interconnected. The member is elongated in a first dimension defining a length that extends between first and second ends of the member, and the member has a second dimension transverse to the first dimension that is smaller than the length. The member defines four, six, or seven holes.

The details of one or more implementations are set forth in the accompanying drawings and the description below. Other features, objects, and advantages of the disclosure will be apparent from the description and drawings, and from the claims.

BRIEF DESCRIPTION OF THE DRAWINGS

FIGS. 7A and 7B are perspective views of an additional embodiment of a fixation device.

DETAILED DESCRIPTION

Figure 1A:
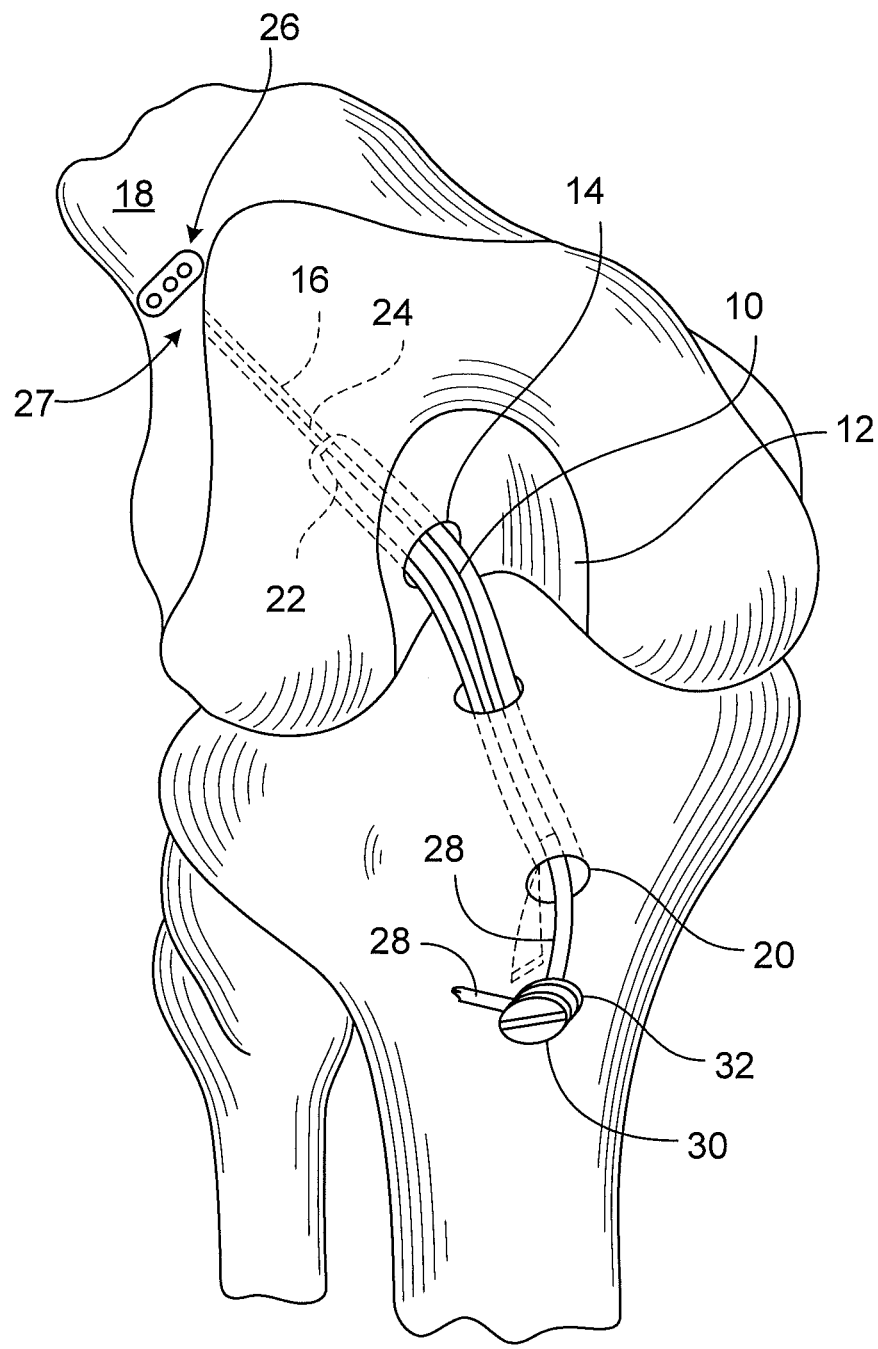
FIGS. 1A and 1B are illustrations of a tissue graft secured within the knee by a graft fixation member.
Figure 1B:
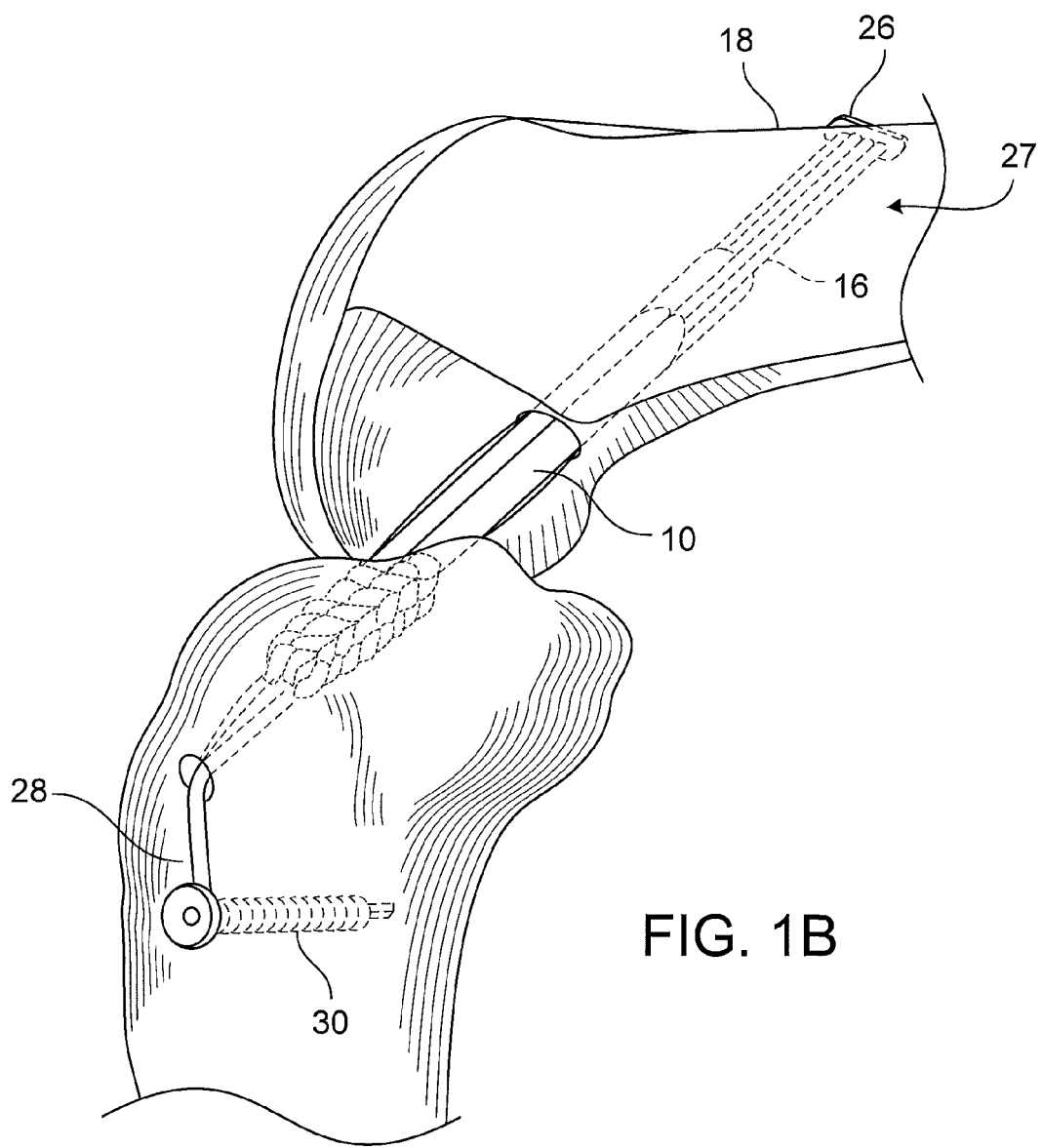

Referring to FIGS. 1A and 1B, a knee joint has a tissue graft 10 (e.g., a patellar tendon graft (FIG. 1A) or a semitendonosis and gracilis graft (FIG. 1B)) implanted in an anterior cruciate ligament (ACL) repair and reconstruction procedure. Prior to implanting tissue graft 10, a notchplasty procedure is preferably performed to expand the intercondylar notch 12 of the femur bone. A femoral channel 14 for receiving one end of tissue graft 10 is then drilled from notch 12 a predetermined distance within the femur with a passing channel 16 of reduced diameter drilled further through the femur from femoral channel 14 to a region of femoral cortex 18. A tibial channel 20 for receiving the other end of tissue graft 10 is drilled from an anterior region of the tibia to a region near the opening of femoral channel 14.

In the case of patellar tendon graft, one end of tissue graft 10 includes a bone block 22 which is shaped and sized in close conformity with femoral channel 14 to ensure optimal healing. A length of suture 24 has one end attached to bone block 22 and the other end secured at femoral cortex region 18 with a graft fixation member 26 of a fixation device 27. The suture 24 is attached to the graft fixation member 26 in a manner that permits the length of the suture 24 between the graft fixation member 26 and the tissue graft 10 to be adjusted prior to or after the graft 10 and the fixation member 26 have been positioned as shown in FIGS. 1A and 1B. The other end of tissue graft 10 includes a second length of suture 28 which is attached to the tibia, for example, with a fixation screw 30. A washer 32 either attached to or positioned under the head of fixation screw 30 helps in holding the suture in place when screw 30 is tightened.

The graft fixation member 26 is positioned using pull threads (not shown) attached to the member. The pull threads are passed through the channels 14 and 16 from the notch 12 to the cortex 18 and used to pull the graft fixation member 26 through the channels 14 and 16 with a long axis of the graft fixation member aligned with the channels. After exiting the channel 16, the pull threads are used to flip the graft fixation member 26 so that the member 26 lies flat against the cortex.

Figure 2:
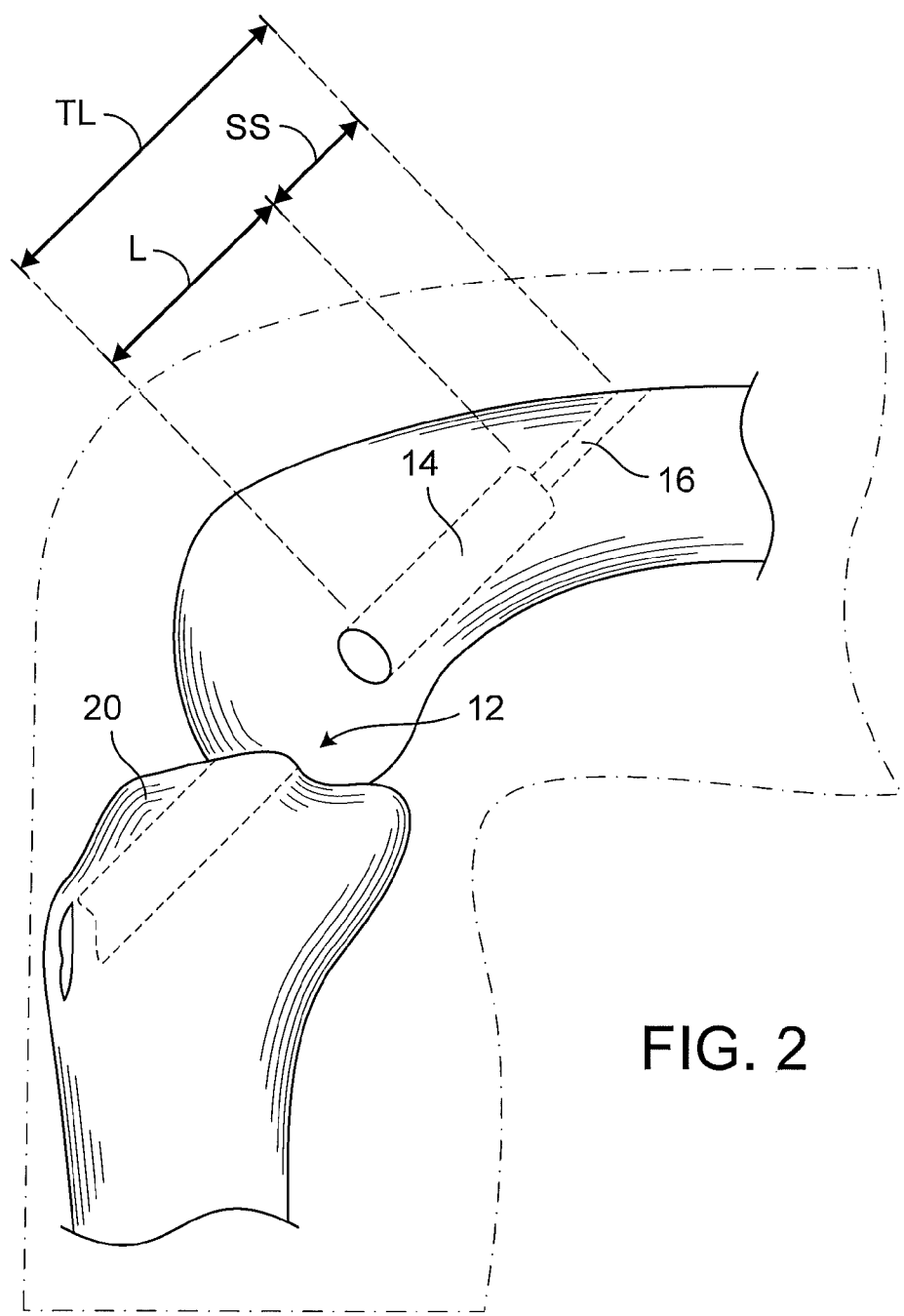
FIG. 2 is another view of the knee joint of FIG. 1.

Referring to FIG. 2, length (L) of femoral channel 14 is selected by the surgeon in accordance with the length of bone block 22 and the desired insertion distance of tissue graft 10 within the femur. The span of suture 24, designated as SS, is approximately that of passing channel 16 so that the sum of the desired insertion length (L) and span of suture (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

The ability to adjust the length of the suture 24 allows the length of the suture span (SS) to be minimized, only being limited by the desired length of passing channel 16. There is a minimum length of the suture 24 that is necessary during passage of the graft fixation member 26 through the channel 14, 16 to allow the member 26 to be positioned in alignment with the channels. Once the graft fixation member 26 is located against the femoral cortex 18, the length of the suture 24 can be shortened by pulling on the suture to maximize the amount of the tissue graft 10 that is located within the femoral channel 14.

Figure 3:
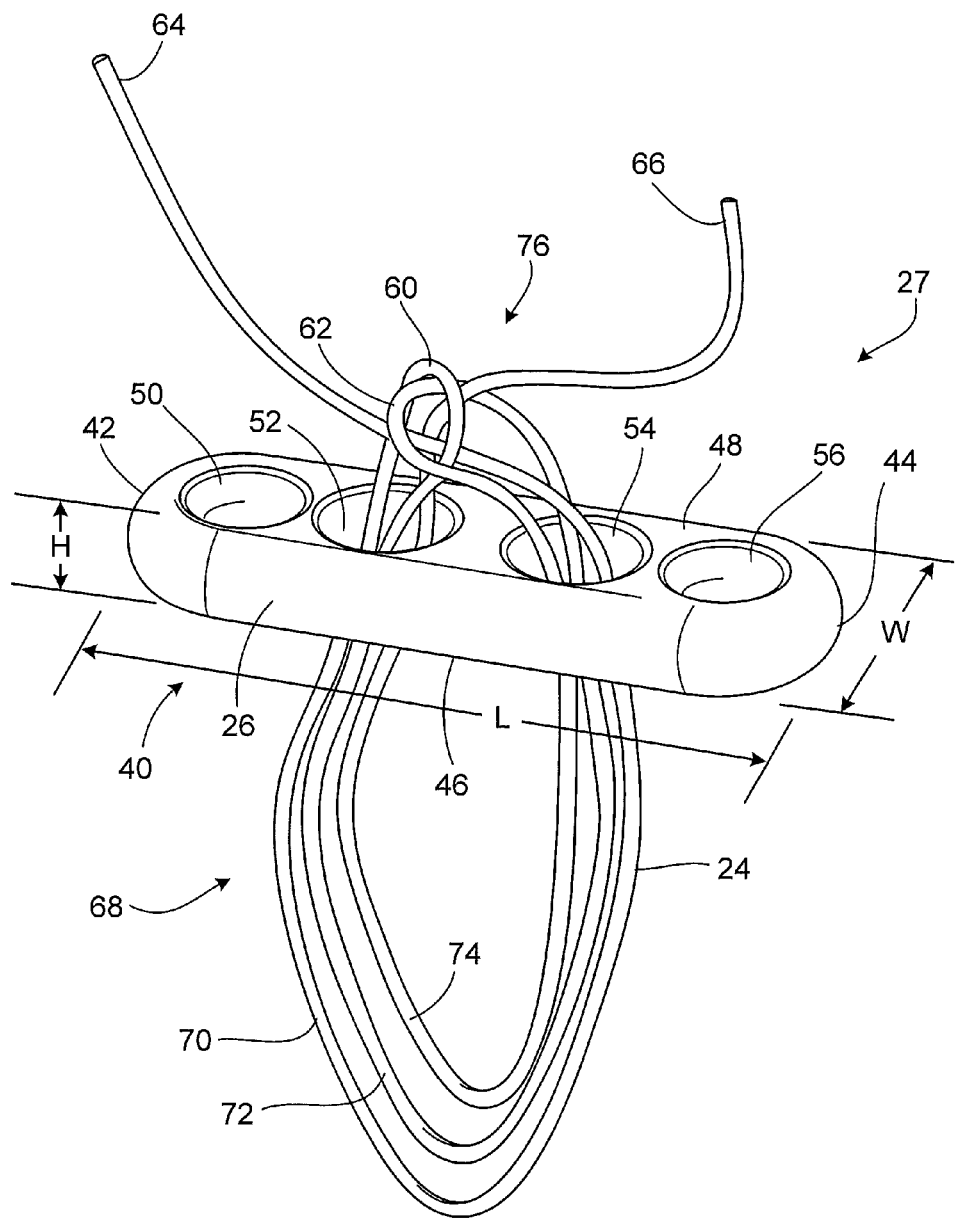
FIGS. 3-6 are perspective views of embodiments of fixation devices.

The suture 24 is a woven or braided suture, for example, #5 Ultrabraid suture, attached to the graft fixation member 26 in a loop and knot configuration to form a fixation device 40. Referring to FIG. 3, the graft fixation member 26 is elongated in a first dimension defining a length, L, that extends between a first end 42 and a second end 44 of the member 26, a second dimension transverse to the first dimension that has a width, W, smaller than the length, L, and a third dimension transverse to the first and second dimensions that has a height, H, small than the length, L. The graft fixation member has a bone contacting side 46 and an opposite side 48. Extending between the sides 46, 48 are four holes 50, 52, 54 and 56. The holes 50 and 56 receive the passing sutures, not shown.

The suture 24 is a single length of suture passed through holes 52 and 54 to form two interconnecting loops 60, 62 through which ends 64, 66, respectively, of the suture 24 are passed, created a knot 76 and a loop 68 of three suture loops 70, 72, and 74. To form the loop and knot configuration, for example, the end 66 of the suture 24 is passed down through hole 54 and up through hole 52, creating loop 70; folded over on itself, around the length of suture extending up from hole 54, and passed back down hole 52, creating loop 60; passed up through hole 54, creating loop 72; passed through loop 60, folded over on itself, and passed back down hole 54, creating loop 62 interconnected with loop 60; passed up through hole 52, creating loop 74; and then passed through loop 62.

By pulling on the ends 64, 66 of the suture 24, the length of the loop 68 can be adjusted, for example, from a minimum that equals the distance between the holes 52 and 54 to about 30 mm, such that, with the tissue graft 10 attached the suture 24, the distance between the graft fixation member 26 and the tissue graft 10 can be adjusted between 0 mm and about 15 mm.

When the fixation device 40 is used with a semitendonosis and gracilis graft (FIG. 1B), the suture 24 can be provided to the surgeon pre-tied to the graft fixation member 26, and operating room personnel attach the tissue graft to the fixation device 40 by passing the tissue graft through the suture loop 68. When a patellar tendon graft (FIG. 1A) is used, operating room personnel form the loop and knot configuration by passing the suture through the bone block of the graft while forming the loop and knot configuration.

The distance between the graft fixation member 26 and the tissue graft 10 can be adjusted while the graft/fixation member construct is in the femoral tunnel. Alternatively, the distance is determined by the surgeon prior to placing the graft.

Once the graft fixation member 26 and the tissue graft 10 are positioned in the knee with the desired length of the suture 24, tension placed on the suture by the tissue graft acts to secure the loop and knot configuration.

The length, width and height of the fixation member 26, is for example, 12 mm×4 mm×1.5 mm.

Other embodiments are within the scope of the following claims.

Figure 4:
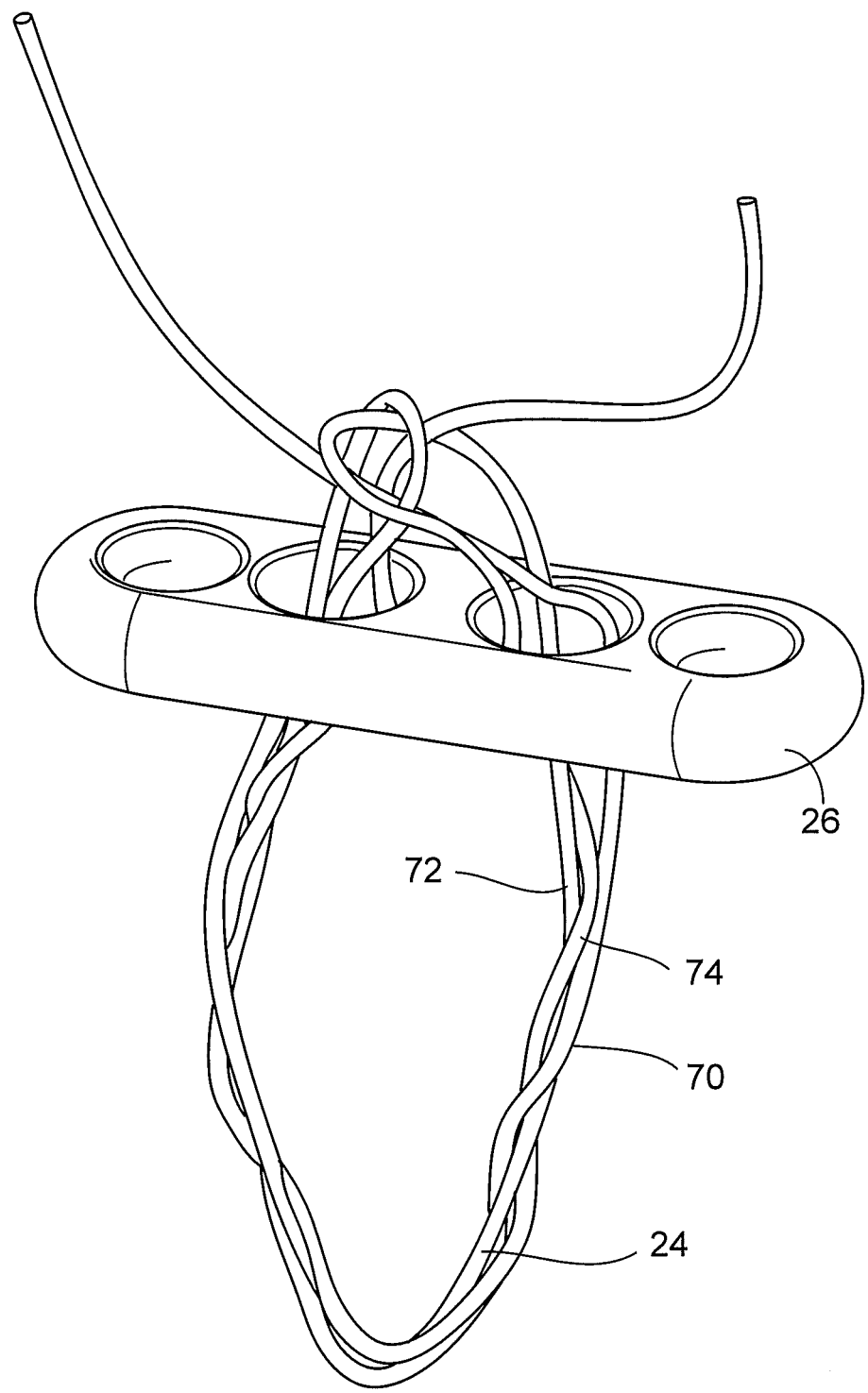
Figure 5:
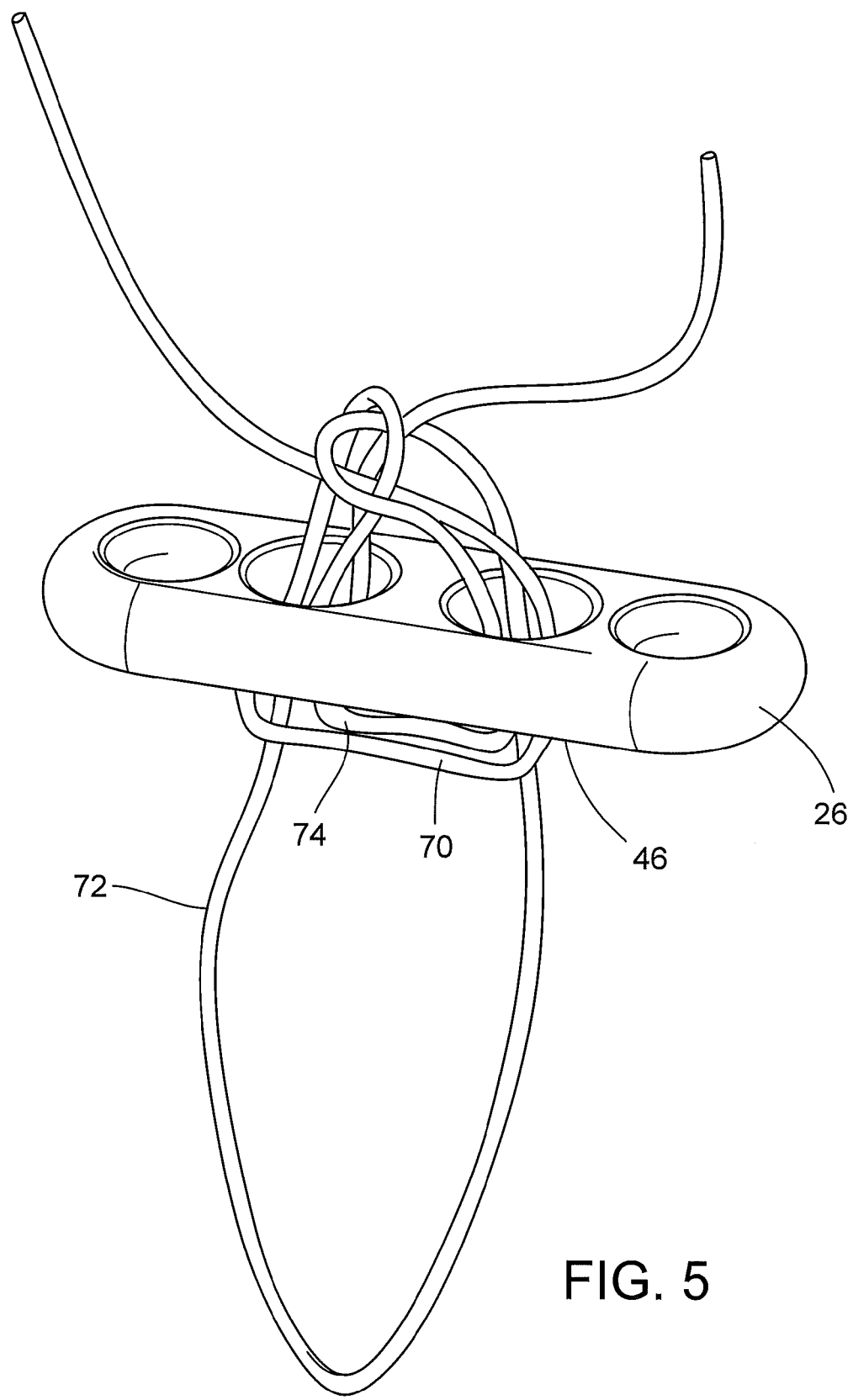
Figure 6:
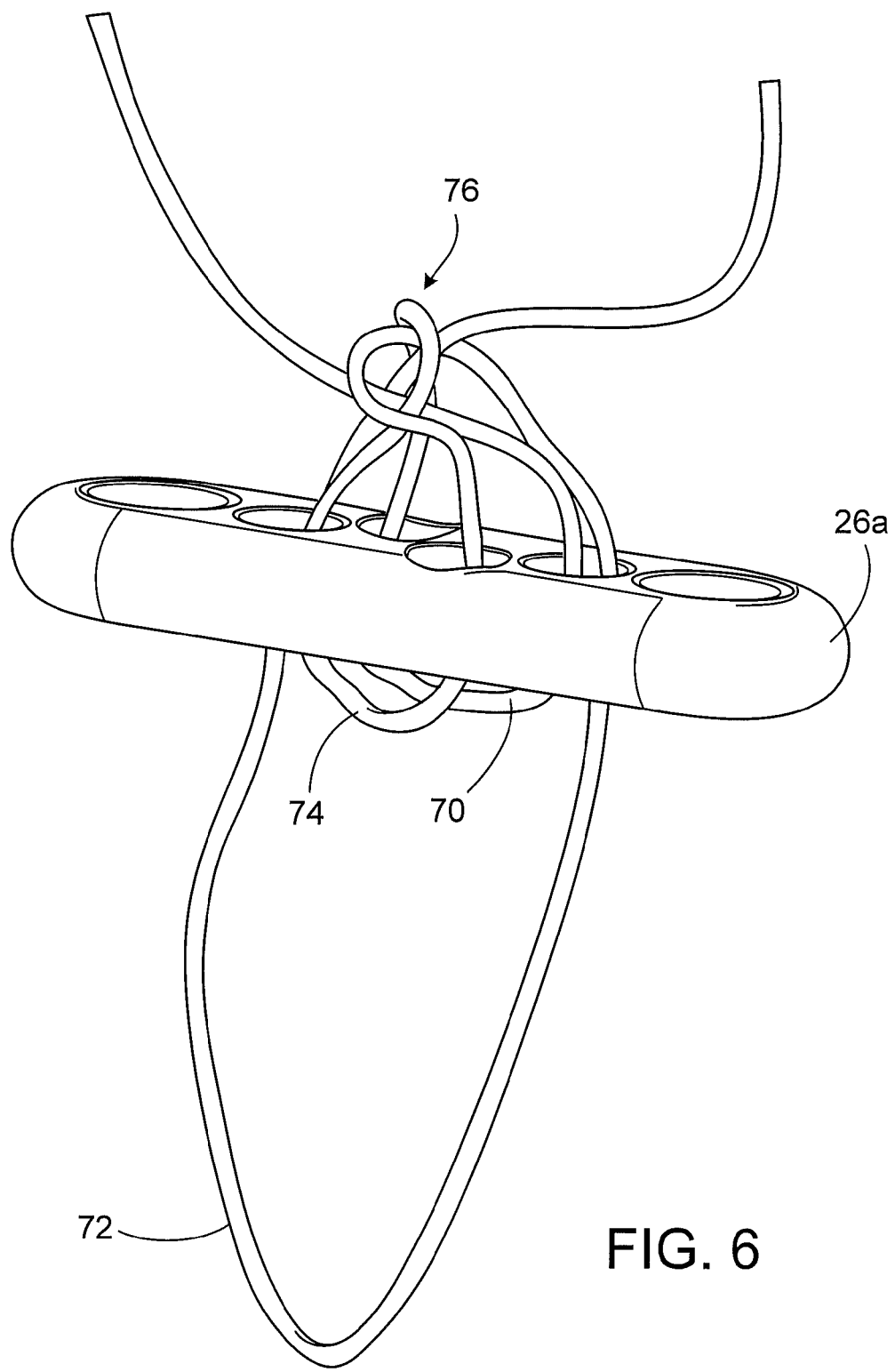

For example, referring to FIG. 4, the suture loops 70, 72 and 73 can be twisted. Referring to FIG. 5, the suture loops 70 and 74 can be tightened against the bone contacting side 46 of the graft fixation member 26 such that in use the tissue graft is only attached to loop 72. The graft fixation member 26a of FIG. 6 includes six holes with the suture 24 being passed through four central holes to form loops 70, 72 and 74, and knot 76. The graft fixation member 26b of FIGS. 7A and 7B includes seven holes with the suture 24 being passed through five central holes 80, 82, 84, 86 and 88. The form the suture construct, the suture end 66 is passed down through hole 88, up through hole 86, over the suture extending up from hole 88, down through hole 84, looped and passed back up through hole 84, down through hole 82, up through hole 80, and through the loop formed between holes 84 and 82.

The graft fixation member can be modified to aid flipping of the member by providing open or closed ends, and variation in thickness, length or width. To aid in positioning the graft fixation member at the end of the channel, the member can have a banana shape or modifications such as rectangular, triangular or other geometric shapes. To aid in strength of pull out the thickness of the graft fixation member between the holes in the member can be adjusted. This section of the graft fixation member between the holes can be modified by increasing or reducing its thickness to open the space for and reduce the distance between the graft fixation member and the tissue graft.

The graft fixation member can include only a single opening with the suture tied to graft fixation member by passing the suture through the single opening in the member to form two suture loops through which ends of the suture pass.

Other implementations are within the scope of the following claims.

What is claimed is:

1. A fixation device comprising:
a member defining at least one opening; and
a suture comprising a knot and loop configuration tied to the member, the suture tied by passing the suture through the at least one opening in the member to form two suture loops through which ends of the suture pass;
wherein the knot and loop configuration is created by passing an end of the suture down through a second opening and up through a first opening, creating a first suture loop; folding the suture over on itself, around the length of suture extending up from the second opening, and passed back down the first opening, creating a first interconnecting loop; passing the suture up through the first opening, creating a second suture loop; passing the suture through first interconnecting loop, and folding the suture over on itself, and passing the suture back down the second opening, creating another interconnecting loop interconnected with the first interconnecting loop, passed up through the first opening; and creating third suture loop, and passing the third suture loop through the another interconnecting loop.

2. The fixation device of claim 1 wherein the two suture loops are interconnected.

3. The fixation device of claim 1 wherein the member is elongated in a first dimension defining a length that extends between first and second ends of the member, the member having a second dimension transverse to the first dimension that is smaller than the length.

4. The fixation device of claim 1 wherein the member defines two openings.

5. The fixation device of claim 1 wherein the member defines four openings.

6. The fixation device of claim 1 wherein the member defines six openings.

7. The fixation device of claim 1 wherein the member defines seven openings.

8. A method of securing a tissue graft comprising:

providing a fixation member having a suture tied thereto by passing the suture through at least two openings in the fixation member to form two suture interconnecting loops through which ends of the suture are passed and creating a knot and loop configuration of three suture loops;

wherein the knot and loop configuration is created by passing an end of the suture down through a second opening and up through a first opening, creating a first suture loop; folding the suture over on itself, around the length of suture extending up from the second opening, and passed back down the first opening, creating a first interconnecting loop; passing the suture up through the first opening, creating a second suture loop; passing the suture through first interconnecting loop, and folding the suture over on itself, and passing the suture back down the second opening, creating another interconnecting loop interconnected with the first interconnecting loop, passed up through the first opening; and creating third suture loop, and passing the third suture loop through the another interconnecting loop;

attaching the suture to the tissue graft; and adjusting the length of the suture between the fixation member and the tissue graft by pulling the suture.

9. The method of claim 8 wherein the providing includes the two suture loops being interconnected.

10. The method of claim 8 wherein attaching the suture comprises forming a loop of soft tissue of the tissue graft over the suture.

11. The method of claim 8 wherein attaching the suture comprises passing the suture through a bone block of the tissue graft followed by tying the suture to the fixation member.

12. The method of claim 8 comprising passing the fixation member, suture, and attached tissue graft through a bone passage, followed by adjusting the length of the suture between the fixation member and the tissue graft.

13. A method of securing a tissue graft, the method comprising:

providing a fixation member having a suture tied thereto, the suture comprising at least one loop comprising a knot and loop configuration of three suture loops created by passing an end of the suture down through a second opening and up through a first opening, creating a first suture loop; folding the suture over on itself, around the length of suture extending up from the second opening, and passed back down the first opening, creating a first interconnecting loop; passing the suture up through the first opening, creating a second suture loop; passing the suture through first interconnecting loop, and folding the suture over on itself, and passing the suture back down the second opening, creating another interconnecting loop interconnected with the the first interconnecting loop, passed up through the first opening; and creating third suture loop, and passing the third suture loop through the another interconnecting loop;

attaching the suture to the tissue graft; and adjusting the length of the suture between the fixation member and the tissue graft by pulling the suture to secure the tissue.

\* \* \* \* \*